(12) United States Patent
Geng

(10) Patent No.: US 7,099,732 B2
(45) Date of Patent: *Aug. 29, 2006

(54) SANITARY SLEEVE OR TIP FOR INTRA-ORAL THREE-DIMENSIONAL CAMERA

(75) Inventor: Z. Jason Geng, Rockville, MD (US)

(73) Assignee: Genex Technologies, Inc., Kensington, MD (US)

(*) Notice: Subject to any disclaimer, the term of this patent is extended or adjusted under 35 U.S.C. 154(b) by 358 days.

This patent is subject to a terminal disclaimer.

(21) Appl. No.: 10/654,193

(22) Filed: Sep. 2, 2003

(65) Prior Publication Data

US 2004/0117052 A1 Jun. 17, 2004

Related U.S. Application Data

(60) Provisional application No. 60/408,040, filed on Sep. 3, 2002.

(51) Int. Cl.
*G06F 19/00* (2006.01)

(52) U.S. Cl. .................................. 700/117; 433/29

(58) Field of Classification Search .................. 700/97, 700/98, 117, 118; 353/7, 42, 8, 123; 707/104.1; 433/29, 2, 30; 356/197, 121, 123, 445; 313/113, 313/501
See application file for complete search history.

(56) References Cited

U.S. PATENT DOCUMENTS

| | | | |
|---|---|---|---|
| 5,527,261 A * | 6/1996 | Monroe et al. | 600/109 |
| 5,675,407 A * | 10/1997 | Geng | 356/147 |
| 5,784,434 A | 7/1998 | Shieh | |
| 6,002,424 A | 12/1999 | Rapa et al. | |
| 6,239,868 B1 | 5/2001 | Jung et al. | |

* cited by examiner

*Primary Examiner*—Kidest Bahta
(74) *Attorney, Agent, or Firm*—Steven L. Nichols; Rader Fishman & Grauer PLLC

(57) ABSTRACT

An intra-oral imaging system includes an optical conduit, a light source generating light rays, at least a portion of which are transmitted through the optical conduit to illuminate a dental surface, a device for converting the light rays into radiation illumination with spatially varying wavelengths prior to illuminating the dental surface, a reflector that directs the light rays from the light source to a selected point; and an imager for receiving the light rays when the light rays are reflected from the dental surface.

29 Claims, 2 Drawing Sheets

SANITARY SLEEVE OR TIP FOR INTRA-ORAL THREE-DIMENSIONAL CAMERA

RELATED APPLICATIONS

The present application claims priority under 35 U.S.C. § 119(e) from the following previously-filed Provisional Patent Applications, U.S. Application No. 60/408,040, filed Sep. 3, 2002 by Geng, entitled "Sanitary Sleeve or Tip for Intra-Oral Three-Dimensional Camera" which is incorporated herein by reference in its entirety.

The present application is related to U.S. application Ser. No. 09/616,723 by Geng entitled "Three-Dimensional Dental Imaging Method and Apparatus Having a Reflective Member." application Ser. No. 09/616,723 is a Continuation-in-Part of U.S. application Ser. No. 09/616,723 by Geng entitled, "Three-Dimensional Dental Imaging Method and Apparatus." Application Ser. No. 09/616,723 claims priority from U.S. Provisional Application. No. 60/144,010, filed Jul. 15, 1999. All three of these previous applications are hereby incorporated by reference in their entireties.

The present application is also related to (1) U.S. Provisional Patent Application No. 60/375,934, "Method and Apparatus for Generating Structural Pattern Illumination" filed Apr. 26, 2002; (2) U.S. Provisional Patent Application No. 60/178,695, "Improvement on the 3D Imaging Methods & Apparatus" filed Jan. 28, 2000; (3) U.S. patent application Ser. No. 09/770,124, "3D Surface Profile Imaging Method & Apparatus Using Single Spectral Light Condition" filed Jan. 26, 2001; (4) PCT Patent Application No. PCT/US01/18644, "3D Surface Profile Imaging Method & Apparatus Using Single Spectral Light Condition" filed Jun. 11, 2001; and (5) U.S. patent application Ser. No. 09/771,531, "Method & Apparatus for 3D Imaging Using Light Pattern Having Multiple Sub-Patterns" filed Jan. 29, 2001. All of these previous applications are hereby incorporated by reference in their entireties.

FIELD OF THE INVENTION

The present invention relates to intra-oral imaging of dental surfaces and to methods and apparatus for such imaging. The present invention also relates to the field of sanitary measures taken for dental instruments.

BACKGROUND

The accurate and rapid intra-oral measurement of dental surfaces for many purposes including the production of prosthodontics or dental parts has been a goal of Dental Science for some time.

A system developed by Francois Duret et al. combines holographic moire techniques to produce an array of three dimensional points that represent a single-view image of a tooth. The hand held optical probe consists primarily of a laser diode and a CCD photo sensor in order to capture dental images. The spatial resolution of the dental images produced with this technique is about 20 µm. Images from different views are then interactively combined, and a rigid theoretical tooth is fitted to the points in order to reconstruct the tooth analytically. With this system, a dental practitioner can personalize the anatomy of a tooth. Further, this system allows design of a custom crown for a particular tooth as well as subsequent milling for immediate fabrication and restoration. The final restoration error is about 80 µm and can produce a posterior crown in less than an hour. However, as mentioned this system requires the use of a laser in the vicinity of a patient's eyes.

U.S. Pat. No. 4,575,805 describes a system called CEREC (Ceramic Reconstruction). According to this patent, the intra-oral scanner incorporates a light emitting diode and lens system to illuminate the cavity of the tooth. The light rays pass through a set of ruled lines, casting stripe patterns on the prepared cavity. A CCD camera is used to record the stripe pattern in a 12.8 $mm^3$ volume. Due to the limitations on the width of the ruled lines, spatial resolution is quite low. To increase the spatial resolution, a mechanism was introduced that requires multiple frame images. Using a piezo motor, the ruler is moved to four fixed and offset locations, allowing the CCD camera to take an image at each of the four locations. The number of measurements is thus quadrupled. In this arrangement, the system loses the capability of taking a complete 3 dimensional measurement in a single snapshot, and the design of the system becomes fairly complicated.

Rekow developed a system known as the Minnesota System. The raw image of a tooth is acquired using a standard 35 mm camera through a 10 mm diameter single rod lens magnifying laryngopharyngoscope. A prism system at the distal end of the rod lens permits the field of view to be 90 degrees. A number of views are used to ensure that complete information is obtained and to minimize the likelihood of blur caused by patient movement. Fiber optics provides the illumination necessary to capture the stereos images, or slides, that are taken on standard photographic film. The slides are then digitized in 4096×4096 resolution. Stereo correspondence algorithms are used to produce three dimensional measurement data. The aim of this system was to produce a low cost high resolution three dimensional measurement. It does not, however, take advantage of the rapid advances in the field of machine vision and analysis.

While each of the above prior art systems has merit in the measurement of dental structure, each have shortcomings of one type or another. Most require multiple imaging which in turn requires that the patient maintain a fixed position for a long period of time. In addition, most of the above systems lack adequate resolution or expose the patient to undesirable radiation such as a laser.

U.S. Pat. No. 5,675,407 to Geng issued Oct. 7, 1997 describes a novel three-dimensional surface profile measuring technique that is able to acquire full frame, dynamic 3-D images of objects with complex surface geometries at high speed. By "full frame 3-D image" is meant that the value of each pixel (i.e. picture element) in an acquired digital image represents the accurate distance from the camera's focal point to the corresponding point on the object's surface. The (x,y,z) coordinates for all visible points on the object surface are supplied by a single 3-D image. By "acquiring dynamic 3-D images at high speed" is meant, that a camera of the type described in U.S. Pat. No. 5,675,407 is able to capture a full frame 3-D image in one snapshot, i.e. within one exposure time of its imager device (for example, within one millisecond), and can obtain a stream of such 3-D images at a sustainable speed of at least 30 frames per second.

SUMMARY

An intra-oral imaging system includes an optical conduit, a light source generating light rays, at least a portion of which are transmitted through the optical conduit to illuminate a dental surface, a device for converting the light rays into radiation illumination with spatially varying wavelengths prior to illuminating the dental surface, a reflector that directs the light rays from the light source to a selected point; and an imager for receiving the light rays when the light rays are reflected from the dental surface.

BRIEF DESCRIPTION OF THE DRAWINGS

The accompanying drawings illustrate various embodiments of the present apparatus and method and are a part of the specification. The illustrated embodiments are merely examples of the present apparatus and method and do not limit the scope of the disclosure.

Throughout the drawings, identical reference numbers designate similar, but not necessarily identical, elements.

DETAILED DESCRIPTION

An intra-oral imaging system includes an optical conduit, a light source generating light rays, at least a portion of which are transmitted through the optical conduit to illuminate a dental surface, a device for converting the light rays into radiation illumination with spatially varying wavelengths prior to illuminating the dental surface, a reflector that directs the light rays from the light source to a selected point; and an imager for receiving the light rays when the light rays are reflected from the dental surface.

In the following description, for purposes of explanation, numerous specific details are set forth in order to provide a thorough understanding of the present method and apparatus. It will be apparent, however, to one skilled in the art that the present method and apparatus may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Improved Intra-Oral Dental Probe and Camera

Figure 1:
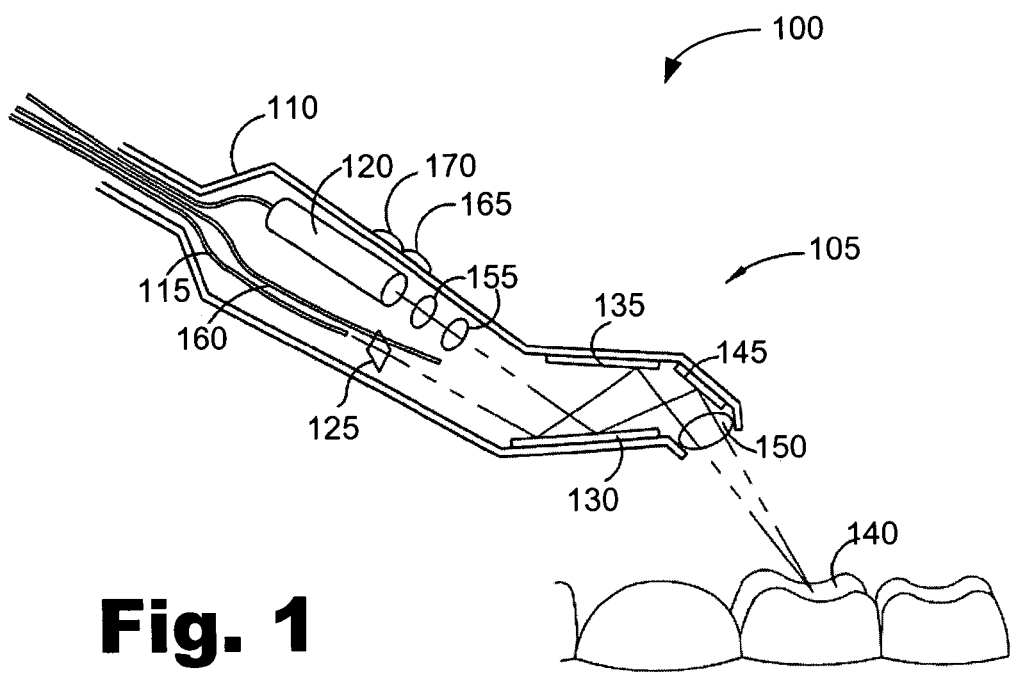
FIG. 1 is a schematic representation of the intra-oral camera of the present invention.

FIG. 1 illustrates an intra-oral imaging system (100) that produces both 3-D and color 2-D images of dental structure. The intra-oral imaging system (100) generally includes an intra-oral probe (105) that is surrounded by an appropriately shaped housing (110) that encompasses a fiber optic bundle (115) and a CCD imaging device (120). A linear variable wavelength filter or LVWF (125) is disposed at the outlet of fiber optic bundle (115). The purpose, composition and utility of this device are described in detail in aforementioned U.S. Pat. No. 5,675,407 and such description will not be repeated herein.

Light projected from fiber optic bundle (115) passes through LVWF (125) and is then reflected from a first mirror (130) to a second mirror (135) onto the surface of dental structure (140) that is to be imaged. Light reflected from the surface of dental structure (140) is then conducted by reflection from a third mirror (145) to the first mirror (130) and onto the CCD imagining device (120). Appropriate lenses or lens pairs (150, 155) maybe incorporated to obtain appropriate focus of the image and protection of the interior of housing (110). The particular shape or configuration of CCD imaging device (120) and housing (110) is not critical to the successful practice of the invention; so long as the configuration of the housing allows for maintenance of a substantially fixed relationship between an output end of the fiber optic bundle (115) and the receiving end of the CCD imaging device (120) during imaging. A configuration in which the parts of the probe (105) remain in a substantially fixed relationship with respect to one another within the housing (110) facilitates generation of a three-dimensional image. In such a configuration, the projection angle θ, described in the '407 patent, remains substantially constant, such that it can be readily related to the different spectral wavelengths produced by a light source which serves to define the x,y,z, coordinates of the three-dimensional image.

A second fiber optic bundle (160) may act as a second independent diverging white light source to permit probe (105) to be used to obtain intra-oral images with accurate color representation for shading, color shadings and shadows. The image is obtained in a similar manner as the three-dimensional image described above. Correct color shading may be important to both the patient and the dentist. Since different parts of the tooth may have different shading and reflection, it is presently an "art" to obtain to obtain a "natural" effect, requiring subtleties in shading and intensity of coloration as well as thickness of materials. Switches (165, 170) permit the selective switching between activation of the fiber optic bundles (115, 160) facilitates the use of the same probe (105) to obtain virtually simultaneously both 3-D and 2-D colored images.

Housing (110) may be fabricated from any suitable material such as a metal or a plastic material, however, for patient comfort plastic or polymeric materials such as polyethylene or polypropylene are preferred as the material of construction. Similarly, fiber optic conduit (115) may comprise a single monolithic light conductor or a bundle of fiber optic fibers. The latter configuration is generally preferred on a cost basis. Suffice it to say for the instant purposes, that LVWF devices are commercially available and well known to the skilled optical artisan. Their operation and the effects they produce are discussed in detail in the foregoing patent. The color ranging principle is not at all restrained by nor does it rely on the LVWF to produce the required radiation. In fact, any means that can provide registered spatial distribution of an energy projection ray that can be related to the wavelength of the ray may be used in the system. Additionally, although the LVWF (125) is depicted as being at the exit of fiber optic bundle (115), it could just as readily be incorporated at the light source described hereinafter.

Improved Intra-Oral Imaging and Dental Fixture Manufacturing System

Figure 2:
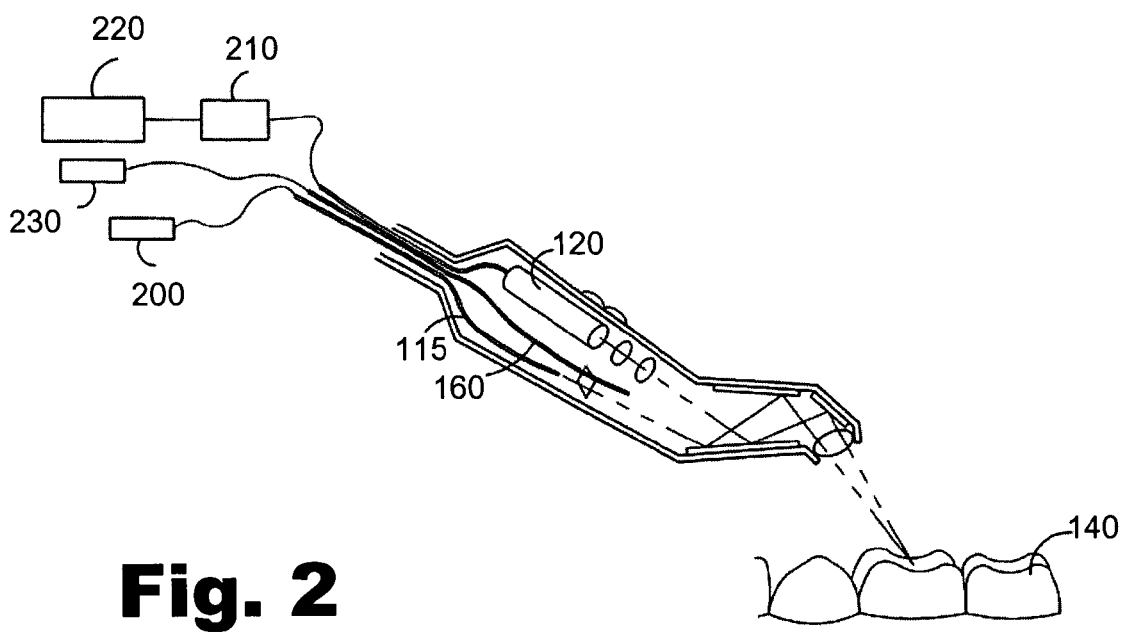
FIG. 2 is a schematic representation of the combined camera, image processing and CAD/CAM system of the present invention.

FIG. 2 illustrates the components external to probe (105) in more detail. A light source (200) is connected to fiber optic bundle (115). Such a light source as described in the '407 patent generates a sheet of white light that passes through a cylindrical lens (not shown) to form a "fan beam" light source. This fan beam light then passes through an LVWF located either ahead of or behind fiber optic bundle (115) to illuminate the dental surface 24 to be "photographed" as described above. The combination of the light source (115) with the LVWF (125) or other similar suitable device produces a bundle of light rays with spatially varying and related wavelengths that are used in the computation and synthesis of the three-dimensional image.

The CCD imaging device (120) is connected to an appropriate host computer (210) containing software for image acquisition, display and processing, three-dimensional computation and data conversion. Such computers and the software for accomplishing these transactions, are well known in the art and/or described in the '407 patent.

The host computer (210) is in turn connected to numerically controlled machine tool (220) such as a rapid prototyping, cutting or milling machinery. Well known CAD/CAM interfaces and control software that generate STL, DXF, SLC and HPP files or other suitable formats and produces a binary file for driving the control electronics of the fabricating equipment are well known in the art. Any appropriate numerically controlled equipment capable of producing the required dental part may be included as fabricating equipment or machinery (220).

The second fiber optic bundle (115) is coupled to a white light source (230) to provide white light for use in two-dimensional color images. Accordingly, the present system is an imaging system capable of capturing both two and three dimensional color images with the use of a single probe.

Operation

In use, a dental part or orthodontic device is produced by intra-orally exposing the dental surface (140) to be addressed by exposure thereof to light emitted from probe (105) and imaging the light reflected from the surface (105) with CCD imaging device (120). The image thus recorded is transmitted to host computer (210) for processing, viewing, archiving, transmission to a distant laboratory, etc. If it is desired to produce a dental part, inlay, onlay, crown filling, braces, orthodontic devices, invisible aligners or bridges etc., data is forwarded to a CAD/CAM file, which in turn produces the binary code, required to control machine tool (220). Machine tool (220) then produces the required dental part.

The system just described has can acquire images in less than about 0.1 seconds and preferably in less than about 0.001 seconds. In addition, it is capable of acquiring video at a rate of at least 30 frames per second (limited only by the capabilities of the CCD device), it is eye safe with its built-in light source when used professionally for its intended purpose, it can simultaneously produce a 2-D image, and is simple and reliable because it has no mechanical moving parts. Further, the present system has a spatial definition that is theoretically virtually infinite and limited only by the spatial and spectral resolution of the CCD imaging technology utilized.

Sanitary Sleeve

Figure 3:
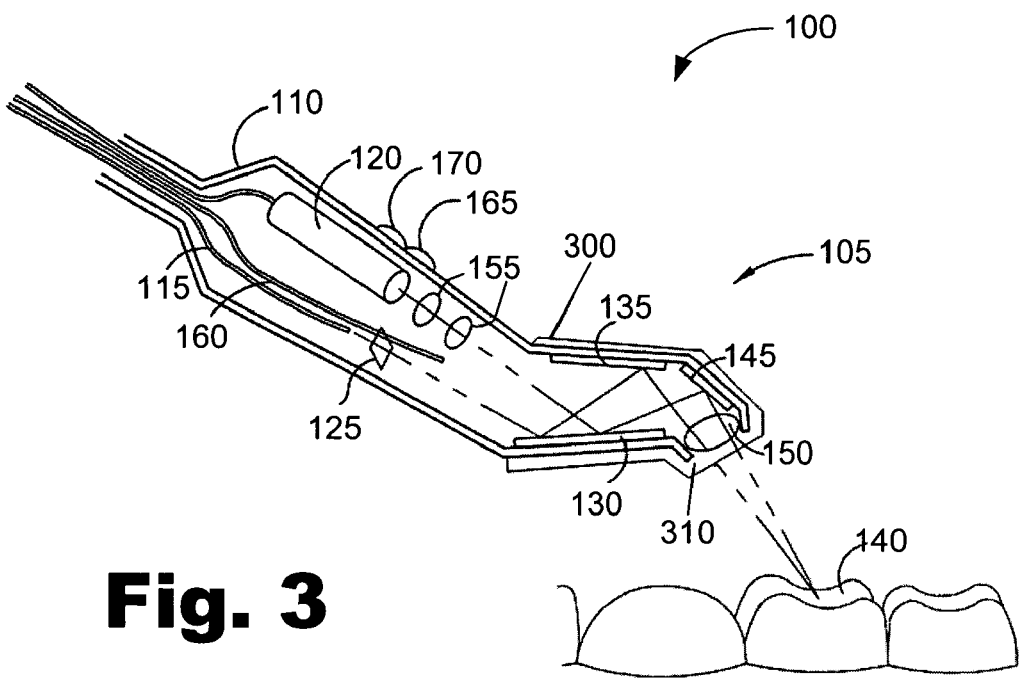
FIG. 3 is a schematic representation of an intra-oral camera with a sanitary sleeve according to a first embodiment of the present invention.

FIG. 3 illustrates an intra-oral imaging system with a sanitary sleeve (300) disposed around the end of the probe (105) that is used in a patient's mouth. The sleeve (300) slips over the end of the camera (105).

The sleeve (300) is held on the end of the probe (105) by friction or by the fingers of the camera-operator (not shown). Consequently, the present sleeve (300) may be readily removed from the camera (105) and a new sleeve can be placed on the camera (105) each time the camera (105) is used on a different patient.

The sleeve (300) may be made entirely of a transparent material that will not interfere with the operation of the camera (105). Alternatively a transparent window (310) may be provided in the end of the sleeve (300) so as to permit imaging of a dental structure (140) in a patient's mouth. The sleeve (300) may be made of a rigid or flexible material, preferably a plastic material such as polyvinyl chloride (PVC). The sanitary sleeve (300) provides for a replaceable sanitary interface that may be replaced for every separate patient, thereby eliminating the likelihood of the transmission of disease from the probe (105)

Replaceable Tip

Figure 4:
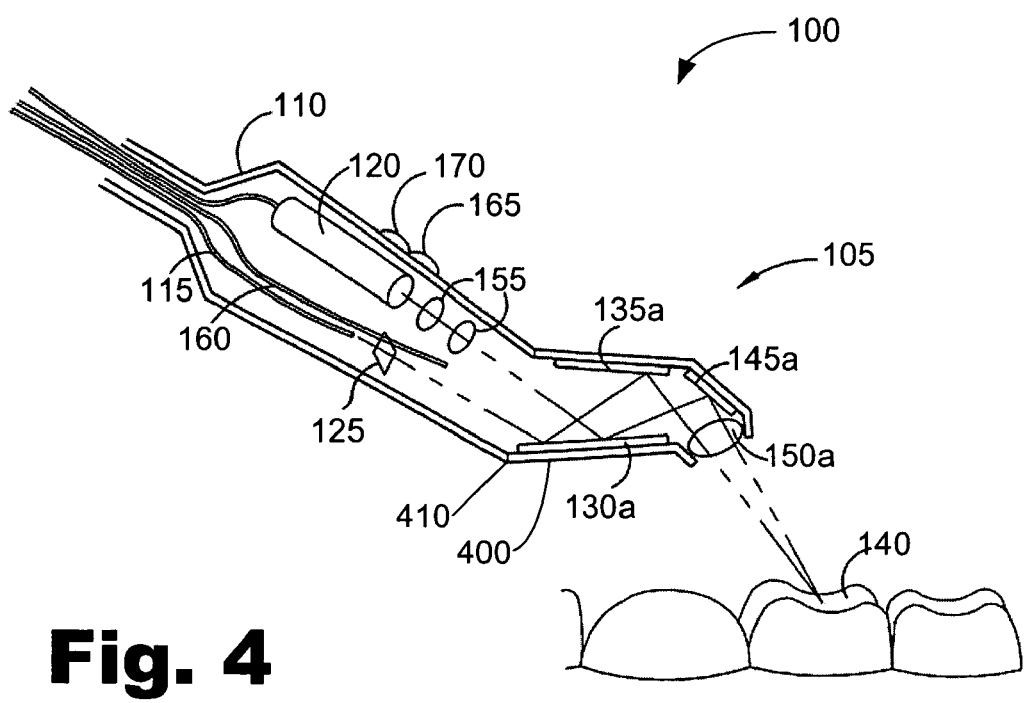
FIG. 4 is a schematic representation of an intra-oral camera with a sanitary sleeve according to a second embodiment of the present invention.

FIG. 4 illustrates a second embodiment. As shown in FIG. 4, the end of the probe (105) may be a sanitary tip (400) that can be replaced each time a new patient is seen. For example, the tip (400) of the probe (105) may be removable and attach to the probe (105) at a joint (410). The tip (400) preferably snaps to the joint (410) to make a tight fit that can, however, be readily broken to allow installation of a new tip.

As shown in FIG. 4, the tip (400) of the probe (105) may house a lens (150a) and mirrors (130a, 135a, 145a) for directing light to, and an image from, the dental work (140) being imaged. The operation of the lens and mirrors is described above and will not be redundantly repeated here. Suitable materials for the tip and housing also have been described above.

After the intra-oral imaging system (100) has been used with a particular patient, the tip (400) can be removed and a new tip installed. Consequently, the spread of disease from one patient to another can be avoided. The tip (400) can be disposable or may be cleansed after each use and then re-used.

The preceding description has been presented only to illustrate and describe the present method and apparatus. It is not intended to be exhaustive or to limit the disclosure to any precise form disclosed. Many modifications and variations are possible in light of the above teaching. It is intended that the scope of the invention be defined by the following claims.

What is claimed is:

1. An intra-oral imaging system comprising:
   an instrument housing;
   an optical conduit running into said housing;
   a light source generating light rays, at least a portion of which are transmitted through said optical conduit to illuminate a dental surface;
   a device for converting said light rays into radiation illumination with spatially varying wavelengths prior to illuminating said dental surface;
   a minor that directs the light rays from said light source to a selected point;
   an imager for receiving said light rays when said light rays are reflected from said dental surface, said reflector being substantially fixed relative to said imager; and
   a sanitary sleeve covering a portion of said intra-oral system that enters a patient's mouth to image said dental surface.

2. The system of claim 1, wherein said optical conduit comprises at least one fiber optic cable.

3. The system of claim 1, wherein said device for converting said light rays comprises an LVWF filter.

4. The system of claim 1, wherein said sanitary sleeve is configured to be selectively removed from said intra-oral system.

5. The system of claim 1, further comprising a sanitary replaceable intra-oral tip portion coupled to said housing.

6. The system of claim 5, wherein said reflector is disposed within said tip.

7. The system of claim 1, wherein a portion of said light rays are projected onto said dental surface without being converted to spatially varying wavelengths.

8. An intra-oral imaging system comprising:
an instrument housing;
an optical conduit running into said housing;
a light source generating light rays at least a portion of which are transmitted through said optical conduit to illuminate a dental surface;
a device for converting said light rays into radiation illumination with spatially varying wavelengths prior to illuminating said dental surface;
a reflector that directs said light rays from said light source to a selected point;
an imager for receiving said light rays when said light rays are reflected from said dental surface; and
a removable tip attached to said housing that is used in a patient's mouth to image said dental surface, said tip being sanitarily replaced for each patient.

9. The system of claim 8, wherein said optical conduit comprises at least one fiber optic cable.

10. The system of claim 8, wherein said device for converting said light rays comprises an LVWF filter.

11. The system of claim 8, wherein a portion of said light rays are projected onto said dental surface without being converted to spatially varying wavelengths.

12. The system of claim 11, wherein said imager comprises a device configured to process two-dimensional and three-dimensional images.

13. The system of claim 12, wherein said imager comprises a CCD camera.

14. A system for manufacturing dental fixtures, comprising:
an intra-oral imaging system having
an optical conduit, a light source generating light rays, at least a portion of which are transmitted through said optical conduit to illuminate a dental surface,
a device for converting said light rays into radiation illumination with spatially varying wavelengths prior to illuminating said dental surface,
a reflector that directs the light rays from said light source to a selected point, and
an imager for receiving said light rays when said light rays are reflected from said dental surface;
a processing device wherein resides software for converting said light rays into image data and manufacturing software for manufacturing a dental fixture based on said image data.

15. The system of claim 14, wherein said optical conduit comprises at least one fiber optic cable.

16. The system of claim 14, wherein said device for converting said light rays comprises an LVWF filter.

17. The system of claim 14, further comprising a housing configured to house said system.

18. The system of claim 14, further comprising a sanitary sleeve covering a portion of said intra-oral system that enters a patient's mouth to image said dental surface.

19. The system of claim 18, wherein said sanitary sleeve is configured to be selectively removed from said intra-oral system.

20. The system of claim 17, further comprising a sanitary replaceable intra-oral tip portion coupled to said housing.

21. The system of claim 20, wherein said reflector is disposed within said tip.

22. The system of claim 14, wherein a portion of said light rays are projected onto said dental surface without being converted to spatially varying wavelengths.

23. The system of claim 14, wherein said manufacturing software is configured to manufacture dental parts.

24. The system of claim 14, wherein said manufacturing software is configured to manufacture orthodontic treatment devices.

25. The system of claim 24, wherein said orthodontic treatment devices comprise invisible aligners.

26. A method of doing business comprising:
selling an intra-oral imaging system comprising;
an optical conduit,
a light source generating light rays that are transmitted through said optical conduit to illuminate a dental surface,
a device for converting said light rays into radiation illumination with spatially varying wavelengths prior to illuminating said dental surface,
a reflector that directs the light rays from said light source to a selected point,
a imager for receiving said light rays when said light rays are reflected from said dental surface; and
separately selling a sanitary sleeve covering a portion of said intra-oral system that enters a patient's mouth to image said dental surface.

27. The method of claim 26 wherein said selling a sanitary sleeve further comprises selling a plurality of sanitary sleeves as a package.

28. A method of doing business comprising:
selling an intra-oral imaging system comprising;
an optical conduit,
a light source generating light rays that are transmitted through said optical conduit to illuminate a dental surface,
a device for converting said light rays into radiation illumination with spatially varying wavelengths prior to illuminating said dental surface,
a reflector that directs the light rays from said light source to a selected point,
an imager for receiving said light rays when said light rays are reflected from said dental surface; and
separately selling a sanitary sleeve covering a portion of said intra-oral system that enters a patient's mouth to image said dental surface.

29. The method of claim 28, wherein said selling a sanitary sleeve further comprises selling a plurality of sanitary sleeves as a package.

* * * * *

UNITED STATES PATENT AND TRADEMARK OFFICE
CERTIFICATE OF CORRECTION

PATENT NO. : 7,099,732 B2  Page 1 of 1
APPLICATION NO. : 10/654193
DATED : August 29, 2006
INVENTOR(S) : Z. Jason Geng It is certified that error appears in the above-identified patent and that said Letters Patent is hereby corrected as shown below:

Column 6, Line 53, Claim 1 "a minor that directs" change to --a mirror that directs--

Column 7, Line 59, Claim 18 "The system of claim 14 changes to --The system of claim 17--

Signed and Sealed this

Twenty-third Day of January, 2007

JON W. DUDAS
*Director of the United States Patent and Trademark Office*